United States Patent [19]

Volesky et al.

[11] Patent Number: 4,769,223

[45] Date of Patent: Sep. 6, 1988

[54] BIOSORBENT FOR GOLD

[76] Inventors: Bohumil Volesky, 471 Berkley Avenue, St. Lambert, Quebec, Canada, J4P 3E7; Nural Kuyucak, 2105 Chomedy, Apt. 11, Montreal, Quebec, Canada, H3H 2A8

[21] Appl. No.: 41,326

[22] Filed: Apr. 22, 1987

[51] Int. Cl.$^4$ ............................................. C22B 11/00
[52] U.S. Cl. .................................. 423/27; 75/118 R; 423/DIG. 17
[58] Field of Search .......................... 423/27, DIG. 17; 75/118 R; 210/601, 620

[56] References Cited

PUBLICATIONS

Tuovinen et al, "Use of Micro-Organisms for the Recovery of Metals", 1974, International Metallurgical Reviews, vol. 19, p. 28.
Nakajima et al, "Studies on the Accumulation of Heavy Metal Elements in Biological Systems", 1981, European Journal of Applied Microbiology and Biotechnology, vol. 12, pp. 76–83.
Mattiasson, "Immobilization Methods", 1982, Immobilized Cells and Organelles, ch. 2, pp. 4–19.
Sloan et al, "Removal of Metal Ions from Wastewater by Algae", 1984, Proc. Industrial Waste Conference, Sec. 9, Metal Wastes, pp. 423–429.
Parkinson, Gerald, "Metals Recovery Makes Big Splash in Canada", Sep. 30, 1985, Chemical Engineering, pp. 19–25.

Primary Examiner—John Doll
Assistant Examiner—Wayne A. Langel
Attorney, Agent, or Firm—Mason, Fenwick & Lawrence

[57] ABSTRACT

Gold ions are removed from aqueous solution or suspension by treatment of aqueous material with biomass derived from the genus Sargassum (e.g.: Sargassum natans), a brown sea-water alga. The process can be utilized to remove gold from industrial or natural waters.

24 Claims, 1 Drawing Sheet

BIOSORBENT FOR GOLD

FIELD OF THE INVENTION

This invention relates to metal ion separation processes and more particulary to processes of extraction of specific ions of or containing gold from waste industrial or natural liquid.

BACKGROUND OF THE INVENTION

Gold was one of the earliest metals available to man due to the relative ease with which large particles of gold can be recovered.

Alluvial gold, or particles found in sand and silt, can be recovered by a density gradient separation technique. Gold is a heavy element which settles faster than other lighter particles. This facilitates its recovery when it reaches the bottom of the recovery "apparatus" as the first species. Ore may be recovered in a similar fashion but must be crushed first. Both are recovered fairly efficiently with current methods.

There are problems, however, in extraction of gold from lower grade ores, waste-rock dump materials, slime-dam residues and scrap materials, as traditional recovery methods are designed to extract only large, coarse gold deposits. Cyanidation, until recently, has been the only alternative to remove small particles of gold from slime on an industrial scale. As the demand for gold increases, processing of lower grade ores, slime residues, waste solutions containing gold and the like to extract gold therefrom needs to be accomplished with greater efficiency.

BRIEF DESCRIPTION OF THE PRIOR ART

In attempts to improve gold extraction, researchers have turned to other methods of gold recovery. Activated carbon has been found to remove gold efficiently from solutions originating from processing of lower grade ores, slime residues, and the like. However, despite good recovery efficiencies, the activated carbon as a processed product is expensive and is relatively soft. Its properties result in a considerable loss of the material during the process of recovery of gold from solutions.

There is, therefore, a need for a simple, inexpensive but efficient means for the extraction of gold from solutions.

The phenomenon of biosorption has been utilized in extraction of metallic species from waste liquids. Living and non-living cells have been used to concentrate metallic anions from their aqueous environment, in what is considered to be a rapid and reversible physical/chemical phenomenon that includes the adsorption of metals in the cellular structure in combination with complexation, ion-exchange, and/or microprecipitation. It is believed that the ion-exchange properties of the natural polysaccharides present in the cell walls may be at least partially responsible.

In European patent publication No. 0094 979 Skagerson discloses a process for the retention of a high concentration of chromium in live yeast cells by intracellular adsorption.

In U.S. Pat. No. 4,320,093 a technique is disclosed for the removal of uranium and thorium cations from solution using a fungal microroganism of the genus Rhizopus.

To enhance the technical and practical application potential of a biosorbent in the metal recovery process, there is the need for an appropriate desorption method, efficiently to release the biosorbent-sequestered metal in a non-damaging, economically feasible fashion to permit re-use of the biosorbent.

Recent research has focused on the investigation of uranium elution and reloading capacities of the *Rhizopus arrhizus* biomass by testing several elution solutions. Sodium bicarbonate was indicated as a suitable eluant. (M. Tsezos, Biotechnol. Bioeng., 23, 973 (1984).

In the recovery of chromium from waste electroplating liquors by ion-exchange on casein, $Cr^{4+}$ was eluted with ammonia and the regeneration of casein was achieved with sulfuric acid, making a repetitive metal extraction cycle possible. (P. T. Davey, M. R. Houchin and G. Winter, Part I. Pilot plant studies. J. Chem. Technol. Biotechnol., 33A, 164 (1983))

SUMMARY OF THE INVENTION

The present invention is based upon the discovery that biomass produced as the result of growth of certain selected marine algae, of the genus Sargassum has an outstanding and totally unexpected ability for selective sorption of gold ions from aqueous solution or suspension. By the term "biomass" as used herein is meant the cellular mass of the (micro)organism produced as a result of growth (of e.g. the alga).

Thus according to the present invention, there is provided a process for the selective extraction of gold from aqueous solution or suspension which comprises contacting an aqueous solution or suspension containing gold, with a biomass derived from marine alga of the genus Sargassum. Perferably, the gold is subsequently desorbed from the biomass by contact with a suitable eluant. Such an eluant should efficiently release the gold from the biomass with little or no damage to the biosorbent material, so that the biosorbent material may be re-used.

DESCRIPTION OF THE PREFERRED EMBODIMENTS

Figure 1:
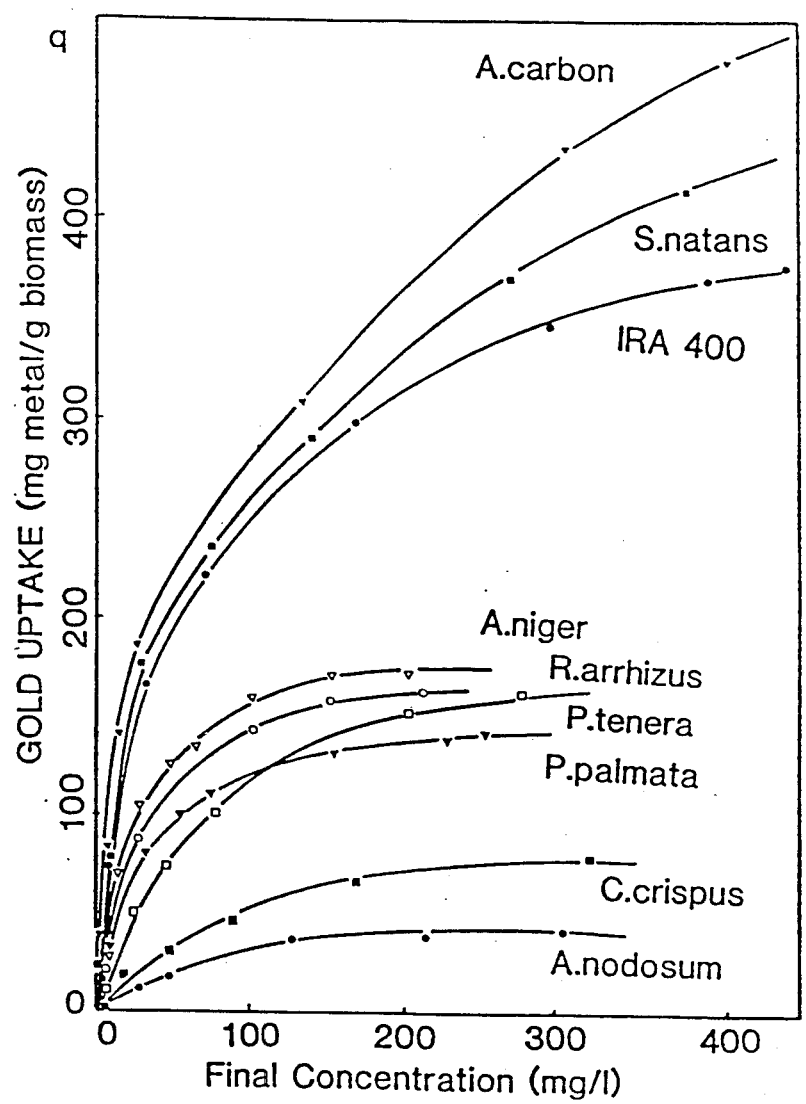

The family of brown algae contains also large marine plants, seaweeds, that are widely distributed throughout the oceans. The biomass for use in the present invention is obtained by collecting and drying the alga in the conventional way.

Many genera of algae are known, including Sargassum, Palmaria and Ascophyllum. Biomass from the particular genus Sargassum is advantageous for present purposes. It gives vastly and unexpectedly better results in gold removal than biomass derived from other algae and fungi, and compares favourably with the performance of activated carbon and ion exchange resins in gold accumulation. Species of Sargassum suitable for gold sequestering include *S. natans, S. hystrix, S. fluitans, S. platicarpum, S. vulgare, S. horneri, S. pilipendula,* and *S. lendigerum.* In particular *S. natans* has been found to possess an impressive maximum gold uptake in excess of 420 milligrams per gram of biosorbent biomass.

It is presently not completely understood why this biomass should be so effective in the accumulation of gold ions from solution. As will appear from the specific examples reported below, species of other genus of brown alga, red alga and fungi are clearly not as effective.

The $[AuCl_4]^-$ form of gold is not stable in solution and is easily hydrolyzed to such ionic species as $[Au^+Cl_2]^-$ and $[Au^{3+}Cl_4]^-$ in water at low pH values. Electrophoretic mobility measurements revealed that the charge on the biomass of S. natans is negative at high pH values. As the pH is lowered, there is an ensuing positive charge in the zeta potential. The negative charge magnitude decreased sharply at around pH 3. It can therefore be hypothesized that the uptake mechanism of gold involves the electrostatic attraction of anions to the positively charged functional groups on the biomass at low pH values.

Although the biomass constitutes the active ingredient of the biosorbent, the biomass may be associated with chemicals or agents to attain properties which are more desirable for practical applications. (e.g.: stiffness, particle size, porosity, etc. . . ). These chemicals or agents provide a solid, porous support for the biomass that is substantially permeable to the gold-bearing solution.

Preferably, the biomass is used in conjunction, e.g. entrapped in a suitable, inert support by homogeneously mixing the biomass and the support. Alternatively, the biomass can be encapsulated in or extruded with the support. Suitable supports include natural polymers such as gels (alginates, agar or carageenan), and polysaccharides such as cellulose, synthetic polymers such as polyamides, acrylics or polystyrene, cellulose nitrate and the like, compounds such as vinylbenzene, and suitable derivatives thereof.

The cellular biomass material used in the process of the invention is a solid, dried and crushed particulate material, which is substantially insoluble in water. When native algae are collected, their biomass is suitably dried and ground to a desirable particle size. Optionally the biomass may then be put into conjunction with, e.g. entrapped in, encapsulated by or extruded with a suitable support as mentioned above. In the practice of the invention, the so-prepared biomass can be used to treat the liquid solution or suspension containing metallic anions in any suitable manner giving good intimate contact between biomass and solution. Thus, the liquid and biomass may be contacted in a holding tank or vessel, under agitation for a suitable contact time, and then separated by conventional means (settling, filtration, etc...). Alternatively, the so-prepared biomass may be used in a packed bed, a pulsed bed or fluidized bed arrangement, a horizontal bed or a vertical column. The ion-containing solution may then be caused to flow through the arrangement contacting the biosorbent biomass.

The initial concentration of the gold in the solution does not effect the biosorptive gold uptake by the biomass as judged in the contact process equilibrium. It appears that even at very low concentrations the biomass will accumulate the gold although the rate will be less than at a higher initial concentration.

A combination of thiourea and ferric ammonium sulfate is preferably used as the eluant for gold desorption. This eluant allows a high recovery of gold with the least possible damage to the biosorbent properties of the biomass. KOH, KCN in alkaline solution, thiourea at both acidic and alkaline pH and a combination of $CaCO_3$ and KOH also can be used to release gold from the biomass, but they have been found on occasion to be harmful to the biomass structure and therefore are not preferred eluants.

Desorption of gold using thiourea and ferric ammonium sulfate is achieved by contacting S. natans biomass and said eluant under agitation in a holding tank or vessel for a suitable period of time, approximately 15 hours or less being desired for optimal gold desorption. Similarly to the gold uptake process, the vertical column or horizontal bed can be used for contacting the metal-laden biosorbent with the eluting solution which, when it leaves the system, contains the formerly sorbed gold. The preferred concentration range of the eluant mixture is 0.05 to 0.2 M thiourea and 0.001 to 0.1 M of ferric ammonium sulfate. The preferred concentration of the eluant mixture is 0.1 M thiourea and 0.02 M ferric ammonium sulfate, although the other described concentrations are also suitable.

There is no substantial loss in the dry weight of the biomass due to treatment with this eluant, nor is there any change, as seen by electron microscopy, in the architecture of the algal cell or its cellular materials.

Thiourea provides sulfur and nitrogen ligands as bonding sites for gold anions. The addition of ferric ammonium sulfate as an oxidizing agent helps to make the sorption reaction reversible and bring the gold back to solution as completely as possible.

The temperature at which sorption and desorption occur does not seem to be critical over a fairly wide range of liquid water temperatures. Temperatures from 4°–50° C. seem to be quite satisfactory.

The pH of both the sorption and desorption solutions can similarly vary over certain limits, although differences in performance are observed at different pH levels. It is advisable, when the sorption solution contains gold in a chloride form, to avoid an alkaline pH extreme, and work in the pH range of about 1–8. In this case the preferred pH operating range for sorption using S. natans is about pH 5, optimally below pH 3.

When gold is present in the sorption solution as a cyanide complex, it is advisable to work in an alkaline pH range. In this case, the preferred pH for sorption using S. natans is about pH 7, optimally above pH 8.5.

The optimum pH for desorption is about pH 5.

The process of the invention is effective to remove gold from aqueous solutions or suspensions thereof. Processing of lower grade ores, waste-rock dump materials, slime-dam residues and scrap materials is made both logistically and economically feasible with this technique.

EXAMPLES

Biomasses from a variety of natural samples were tested for their ability in selective absorption of gold ions from aqueous solutions under a variety of different conditions.

The algal biomass samples were collected, sun-dried and further dehydrated in an oven at 60° C. They were then washed twice with deionized distilled water and dried again. The powdered product was obtained by grinding the biomass in a blender for approximately 3 minutes.

Fungal biomass samples of *Rhizopus arrhizus* and *Aspergillus niger* were washed with distilled water and dried at a temperature below 90° C.

Test solutions of gold were obtained by dissolving exact quantities of $NaAuCl_4.2H_2O$ in deionized distilled water.

In order to control the pH of the solutions, additions of 0.1 N HCl or 0.1 N NaOH were made.

The experimental laboratory contacting procedure is to add a known quantity of biomass to an initial gold solution which has a known concentration of gold. The biomass in solution is mixed using, for example, a magnetic bar mixer or by placing the container on a rotary shaker. The biomass is left in contact with the solution for a given period of time, (in the specific experiments, 16 hours), to allow thorough metal pick-up. Then, the biomass is filtered out from the suspension and the filtrate re-analyzed to determine the residual concentration of the test metal ion, to determine the amount and efficiency of the biosorption. The experiments were repeated several times using different quantities of biomass.

Separation of the biomass sample from the solution at the end of each contact period was accomplished by vacuum filtration. Millipore membrane filters with a 0.45 micrometer average pore diameter were used. Each one was, however, before use, washed with distilled deionized water and the first 10 ml of filtrate was discarded in order to minimize possibilities of change of the equilibrium gold concentration due to retention by the filter membrane or complexation by washable total organic carbon.

To confirm the accumulation of gold on the biomass following the biosorption contact, the metal-laden biomass was digested with aqua regia solution. A Perkin-Elmer (model 403) atomic absorption spectrometer was used to determine the concentration of Au in solution.

The redox potential was measured with a Ag/AgCl electrode and a pH meter. The potentials were determined with a PRA model 273 Potentiostat (EG and C, Princeton Applied Research).

Electrophoretic mobility was measured by using a free flow electrophoresis apparatus (Rank Bros. Mark II).

The sorption isotherms were drawn with the statistical Analysis Sytem (SAS) available on the McGill University System for Interactive Computing (MUSIC).

Experiments were generally performed at 23° C. However, some analysis of gold uptake using S. natans was performed at temperatures from 4°-40° C. to determine the optimum gold uptake temperature. A significant increase in the gold biosorptive uptake was observed when the temperature increased from 4°-23° C.; however, the increase was not considerable in the temperature range of 23°-40° C.

Experiments were conducted at pH values of 1, 2.3, 2.5, 4.0, 4.3 and 6.3 Improved gold uptake was observed at pH values below 3.

More than fifteen different types of eluting solutions were selected and tested at two pH values, acidic and alkaline at room temperature for their desorption capacity of gold. All chemicals used were of analytical grade. Elution was performed using a batch technique whereby samples of metal-laden biomass and eluant were mixed using a rotary shaker (120 rpm) for 24 hours. Vacuum filtration (Millipore 0.45 micrometer filters) separated the biomass and solution at the end of this contact period.

Gold concentration in the solutions was analyzed with an atomic absorption spectrometer. The ratio of loaded biomass weight (in mg) to the eluant volume (in ml) was defined as the solid to liquid ratio and was investigated over the range from 0 to 6 for each eluant.

The eluted biomass retained by the filter membrane was washed with distilled deionized water, dried at 50° C., and reloaded with gold in another sorption cycle.

Electron micrographs of the eluted biomass were made on a Phillips Model 300 transmission electron microscope at an accelerating voltage of 40 Kv.

The pH range that was tested was 1 to 7. Temperatures in the range of 4°-50° C. appeared to be appropriate.

The results of the experiments are presented graphically in the accompanying FIG. 1 and Tables 1 and 2:

FIG. 1 is a plot of the results of experiments performed at pH 2.5 using various concentrations of gold in the starting solutions, adding to samples thereof standard quantities of the biomass from two brown sea-water algae, *Sargassum natans* and *Ascophyllum nodosum;* 2 fungi: *Aspergillus niger* and *Rhizopus arrhizus;* 3 red algae: *Porphyro tenera, Palmoria polmata* and *Chondrus crispus,* activated carbon (Calgon Co.) and an ion exchange resin (Ionex IRA-400 available from Rohm and Haas Co.), the different points on the isotherm graph were obtained by use of different initial quantities of biomass or analogous compound. On the horizontal axis is plotted the equilibrium solution concentration ($C_{eq}$) in mg/L. On the vertical axis is plotted the equilibrium metal loadings (q) in milligrams of Au per gram of biomass. From FIG. 1, it can be seen that the biomass of *S. natans* exhibited not only a desirable steep biosorption isotherm and a high maximum loading curve plateaus, but also reduced the equilibrium gold concentration to less than 2 mg/L with a corresponding metal uptake of 50 mg/g. The maximum metal uptake of this alga was in excess of 420 mg/g at pH 2.5.

*S. natans* is clearly superior to other algae and fungi examined for gold sorption and compares favourably with the activated carbon and ion exchange resin.

Comparisons of various eluants at two pH values, at room temperature, on the desorption capacity for gold from the biomass *S. natans* are shown in Tables I and II.

The eluants are assessed by two factors. One is the elution efficiency which is expressed as a percent fraction of the metal loading initially present on the biomass, (A). The other is the resorption capacity which is an indication of the metal uptake capacity exhibited by the biomass after the first elution step as a percent of the original loading, (B). Results were based on the use of a solid to liquid ratio, ie: a ratio of gold-laden biomass to eluant, of 5.

Although several solutions appear to be appropriate eluants to release gold from the biomass (eg: KOH, KCN in alkaline solution, thiourea at both acidic and alkaline pH, and a combination of $CaCO_3$ and KOH), as seen in column A, they are harmful to the cellular structure and therefore limit the reuse potential of the biomass, as seen in column B.

The mixture of thiourea and ferric ammonium sulfate was the best eluant averaging approximately. 98% of the original gold biosorptive uptake capacity.

TABLE 1

GOLD-LADEN *S. natans* BIOMASS
IN THE FIRST BATCH-TYPE ELUTION

| Eluants | $pH_i$ (initial) | $pH_f$ (final) | (A) Elution efficiency (% original capacity) | (B) re-uptake (% original capacity) | Au capacity (B/A) |
|---|---|---|---|---|---|
| 0.1 N $NO_3^-$ | 4.3 | 3.9 | 43 | — | — |
| 0.1 N $SO_4^{2-}$ | 4.2 | 3.8 | 22 | — | — |

TABLE 1-continued

GOLD-LADEN S. natans BIOMASS IN THE FIRST BATCH-TYPE ELUTION

| Eluants | pH$_i$ (initial) | pH$_f$ (final) | (A) Elution efficiency (% original capacity) | (B) re-uptake (% original capacity) | Au capacity (B/A) |
|---|---|---|---|---|---|
| 0.1 N H$_3$PO$_4^{3-}$ | 4.3 | 4.0 | 27 | — | % |
| 0.1 M KOH | 11.5 | 10.4 | 87 | 68 | 78 |
| 0.1 M Na$_2$CO$_3$ | 10.9 | 10.5 | 42 | — | — |
| 0.1 M Na$_2$CO$_3$ | 7.7 | 6.9 | 10 | — | — |
| 0.1 M NaHCO$_3$ | 10.5 | 10.2 | 18 | — | — |
| 0.1 M Na$_2$CO$_3$ + 0.1 N KOH | 10.9 | 10.5 | 84 | 63 | 77.7 |
| 0.1 M CaCO$_3$ + 0.1 N KOH | 12 | 10.9 | 81 | 86.5 | 1.03 |
| 0.1 M CaCl$_2$ + 0.1 N KOH | 11.7 | 9.2 | 57 | — | — |
| 0.1 M CN$^-$ | 4.6 | 4.3 | 5 | — | — |
| 0.1 M CN$^-$ | 11.9 | 11.1 | 93 | 6.5 | 7 |
| 0.1 M EDTA | 10.5 | 9.1 | 20 | — | — |
| 0.1 M KBr + 20% EtOH | 11 | 10.2 | 35 | — | — |
| 0.1 M Urea | 3.8 | 5.3 | 62 | 68 | 1.09 |
| 0.1 M Urea | 10.8 | 8.7 | 55 | 51 | 92 |
| 0.1 M Thiourea | 3.9 | 3.2 | 83 | 89 | 1.07 |
| 0.1 M Thiourea | 11.7 | 10.2 | 95 | 71 | 1.07 |
| 1 M Thiourea | 4.3 | 3.7 | 91 | 69 | 75.8 |
| 0.1 M Thiourea + 0.02 M NH$_4$Fe(SO$_4$)$_2$ | 5.3 | 4.4 | 98 | 97.8 | 99 |
| 0.1 M Thiourea + 0.02 M FeCl$_3$ | 4.9 | 4.7 | 98 | 79 | 80.6 |
| 0.1 M Thiourea + 0.02 M Fe$_2$(SO$_4$)$_3$ | 5.2 | 4.8 | 97.5 | 83 | 85 |

Gold-laden biomass at 170 mg/g.
Solid to liquid ratio (S/L) = 5.

TABLE 2

GOLD-LATEN S. natans BIOMASS IN THE SECOND BATCH-TYPE ELUTION

| Eluants | pH$_i$ (initial) | pH$_f$ (final) | (A) Elution efficiency (% original capacity) | (B) re-uptake (% original capacity) | Au capacity (B/A) |
|---|---|---|---|---|---|
| 0.1 M CaCO$_3$ + 0.1 M KOH | 12.1 | 10.9 | 94 | 71.8 | |
| 0.1 M CaCO$_3$ + 0.1 M KOH | 10 | 8.3 | 83 | 73.3 | 86.5 |
| 0.1 M CaCO$_3$ + 0.05 M KOH | 11.7 | 10.8 | 64 | 63.6 | 99.3 |
| 0.05 M CaCO$_3$ + 0.1 M KOH | 11.4 | 10.3 | 79 | 57.9 | 73.3 |
| 0.1 M Thiourea | 10.8 | 6.4 | 87.3 | 73 | 83.6 |
| 0.1 M Thiourea | 3.7 | 3.4 | 84.2 | 77 | 91.4 |
| 0.05 M Thiourea | 10.5 | 8.1 | 52.1 | 49 | 94.0 |
| 0.05 M Thiourea | 4.1 | 3.7 | 67.2 | 57 | 84.8 |
| 0.2 M Thiourea | 4.0 | 3.7 | 84.4 | 65 | 77. |
| 0.1 M Thiourea + 0.001 M Oxidant* | 3.9 | 3.3 | 85.1 | 89 | 1.045 |
| 0.1 M Thiourea + 0.005 M Oxidant | 3.8 | 3.5 | 92.3 | 92 | 99.6 |
| 0.2 M Thiourea + 0.005 M Oxidant | 4.1 | 3.6 | 93.8 | 91 | 97.0 |
| *0.1 M Thiourea + 0.02 M Oxidant | 3.9 | 3.6 | 98.8 | 98.3 | 99.5 |
| 0.1 M Thiourea + 0.05 M Oxidant | 4.1 | 3.7 | 97.3 | 94.2 | 96.8 |
| 0.1 M Thiourea + 0.1 M Oxidant | 3.9 | 3.7 | 94.7 | 93 | 98.2 |

Gold-laden biomass at 170 mg/g.
Solid to liquid ratio (S/L) = 5.
*NH$_4$Fe(SO$_4$)$_2$ = FAS

We claim:

1. A process for the extraction of gold from aqueous solution or suspension which comprises contacting the aqueous solution or suspension containing the gold with an effective amount of biomass capable of effectively sequestering large quantities of the gold to obtain a gold-laden biomass, said biomass being derived from the growth of the marine algae of the genus Sargassum.

2. The process of claim 1 including the step of desorbing the deposited gold from the biomass by contacting said gold-laden biomass with a suitable eluant.

3. The process of claim 1 wherein the biomass is derived from growth of the species *Sargassum natans*.

4. The process of claim 3 wherein solution contains gold in a chloride form and said contacting takes place at a pH below about pH 5.

5. The process of claim 3 wherein solution contains gold as a cyanide complex and said contacting takes place at a pH above about 8.5.

6. The process of claim 2 wherein eluant solution contains thiourea and ferric ammonium sulfate.

7. The process of claim 6 wherein eluant solution is a solution of thiourea and ferric ammonium sulfate, in concentration ranges of 0.05 M to 0.2 M and 0.001 M to 0.1 M respectively.

8. The process of claim 4 wherein said contacting takes place at a pH below 3.

9. The process of claim 2 wherein said step of desorbing occurs at about pH 5.

10. The process of claim 1 wherein the biomass is used in association with a suitable support.

11. The process according to claim 10 wherein said support is selected from divinylbenzene, vinyl acetate and vinyl chloride.

12. The process according to claim 10 wherein said support is a polymer.

13. The process according to claim 12 wherein said polymer is a natural polymer.

14. The process according to claim 12 wherein said natural polymer is a gel selected from alginate, agar or carageenan.

15. The process according to claim 12 wherein said polymer is a synthetic polymer, selected from polystyrene, polyamide, and acrylic polymer, nylon and cellulose nitrate.

16. The process according to claim 10 wherein said biomass is encapsulated in a suitable support.

17. The process according to claim 16 wherein said support is a synthetic polymer selected from nylon, acrylic, and cellulose nitrate.

18. The process of claim 1 wherein the biomass is derived from growth of the species *Sargassum hystrix*.

19. The process of claim 1 wherein the biomass is derived from growth of the species *Sargassum fluitans*.

20. The process of claim 1 wherein the biomass is derived from growth of the species *Sargassum platicarpum*.

21. The process of claim 1 wherein the biomass is derived from growth of the species *Sargassum vulgare*.

22. The process of claim 1 wherein the biomass is derived from growth of the species *Sargassum horneri*.

23. The process of claim 1 wherein the biomass is derived from growth of the species *Sargassum filipendula*.

24. The process of claim 1 wherein the biomass is derived from growth of the species *Sargassum lendigerum*.

* * * * *